United States Patent [19]

Tonelli et al.

[11] Patent Number: 5,124,420
[45] Date of Patent: Jun. 23, 1992

[54] PERFLUOROALKENES AND FLUORINATION PRODUCTS THEREOF

[75] Inventors: Claudio Tonelli, Concorezzo; Vito Tortelli, Milan, both of Italy

[73] Assignee: Austimont S.r.l., Milan, Italy

[21] Appl. No.: 723,279

[22] Filed: Jun. 28, 1991

Related U.S. Application Data

[62] Division of Ser. No. 606,622, Oct. 31, 1991, Pat. No. 5,068,470, which is a division of Ser. No. 348,003, filed as PCT/EP88/00768, Aug. 26, 1988, Pat. No. 5,026,928.

[30] Foreign Application Priority Data

Aug. 27, 1987 [IT] Italy .................. 21726 A/87

[51] Int. Cl.$^5$ .............................. C08F 4/00
[52] U.S. Cl. ..................... 526/206; 526/255
[58] Field of Search .......................... 526/206

[56] References Cited

U.S. PATENT DOCUMENTS 3,066,122 12/1960 Brinker et al. ............... 526/206
3,470,143 9/1969 Schrage et al. ............... 526/206

FOREIGN PATENT DOCUMENTS 0121898 10/1984 European Pat. Off. .
1143599 2/1969 United Kingdom .

OTHER PUBLICATIONS

CA vol. 84, 1976 p. 394, 84:42878g.
Patent Abstract of Japan, vol. 9, No. 108 (C-280) JP60-1143 Published 7 Jan. 1985.
CA vol. 108, 1988 p. 4 108:75928r.
74–Radiation Chem. Photochem. vol. 106, 1987 p. 459 106:25594s.
74–Radiation Chem Photochem vol. 104, 1986 p. 483 104:12922f.
74–Radiation Chem Photochem vol. 98, 1983 p. 589 98:188927h.

*Primary Examiner*—Joseph L. Schofer
*Assistant Examiner*—N. Sarofim
*Attorney, Agent, or Firm*—Stevens, Davis, Miller & Mosher

[57] ABSTRACT

The present invention relates to the synthesis of new terminal olefins, perfluoro 2,4-dimethyl 3-ethylpentene and perfluoro 2-isopropyl 3,3-dimethyl butene, and to the subsequent fluorination thereof in order to obtain highly branched perfluoroalkanes, capable of providing perfluoroalkyl radicals, which are utilizable as initiators for the polymerization of ethylenically unsaturated monomers.

1 Claim, No Drawings

PERFLUOROALKENES AND FLUORINATION PRODUCTS THEREOF

This application is a division of application Ser. No. 07/606,622 filed Oct. 31, 1990 (now U.S. Pat. No. 5,068,470 issued Nov. 26, 1991), which in turn is a division of Ser. No. 07/348,003, filed Apr. 14, 1989 (now U.S. Pat. No. 5,026,928 issued Jun. 25, 1991, which was the U.S. National Phase of PCT/EP88/00768 filed Aug. 26, 1988.

Objects of the present invention are new initiators for the polymerization of ethylencially unsaturated products and in particular of fluorinated olefins. More in particular, the present invention relates to perfluorinated compounds capable of releasing radicals which are highly reactive under the polymerization conditions. Actually, the perfluoroalkyl radicals are very interesting as they do not exhibit the drawbacks caused by inorganic peroxides, such as for example the persulphates, which introduce reactive end groups into the polymer, what requires subsequent expensive treatments in order to convert again the polymer end groups to non-reactive groups (D. I. Mc Cane Encyclopedia of Polymer Science and Technology, vol. 12, pages 623–670).

However, at present, the generators of perfluoroalkyl radicals are often too stable, such as e.g. $CF_3I$, which requires too high utilization temperatures and which could interfere with the polymerization process, thereby causing undesirable drawbacks, or they are too expensive, such as the perfluoroacyl peroxides.

In EP 121,898, by partial fluorination of the $C_3F_6$ trimers, stable perfluoroalkyl radicals are obtained. However, these products are obtained with not very high yields and in admixture with the reaction raw products. Therefore these radicals are little utilizable because the olefins can interfere with the monomers during the polymerization step.

In Italian patent application 20061 A/87 in the name of the Applicant hereof, the hexafluoropropene trimer of formula (I):

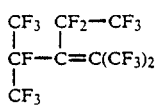
(I)

prepared according to the process described in U.S. Pat. No. 3,917,724 was subjected to fluorination in the presence of U.V. radiation, so obtaining the compounds of formulae (II) and (III):

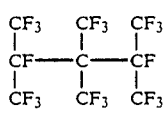
(II)

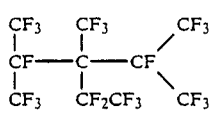
(III)

These perfluoroalkanes, when subjected to temperatures higher than 100° C., decompose, thereby generating perfluoroalkyl radicals, which are utilized in radical polymerization.

Other perfluoroalkanes capable of providing perfluoroalkyl radicals to be utilized as initiators for radical polymerization have now surprisingly been found.

In fact, when the olefin of formula (I) is subjected to U.V. radiation, it isomerizes and provides the terminal olefins of formulas (IV) and (V):

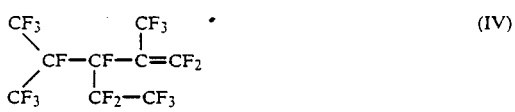
(IV)

(V)

which, when subjected to fluorination, give rise to the perfluoroalkanes of formulas (VI) and (IX):

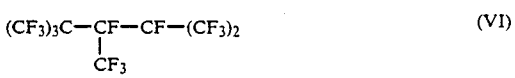
(VI)

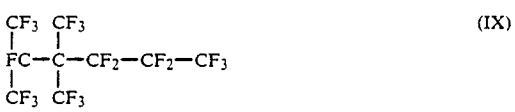
(IX)

which, since they are highly ramified, are capable of generating perfluoroalkyl radicals at temperatures higher than 100° C.

The isomerization reaction is generally conducted at room temperature by irradiating with U.V. radiation (the source of which is a high pressure Hg-vapor lamp type Hanau TQ 150 W) the perfluoroolefin of formula (I); the reaction raw product is then purified by rectification.

The further fluorination reaction to obtain the compound of formula (VI) and of formula (IX) from perfluorooilefins (IV) and (V) is generally conducted at room temperature, by introducing, at the beginning, the fluorine diluted with an inert gas and by gradually raising the fluorine flow as the reaction proceeds. The products of formulas (VI) and (IX) are isolated by rectification.

By the process according to the invention, besides the mentioned perfluoroalkanes, other perfluoroalkanes are obtained, in particular the product (VIII), which, however, is not utilizable as a generator of radicals.

Furthermore, the perfluoroolefin of formulas (IV) and (V) according to the present invention, besides being useful intermediates for the preparation of perfluoroalkanes utilizable as sources of perfluoroalkyl radicals, prove to be advantageous starting products for the preparation of fine chemicals.

The following examples are given merely to illustrate the present invention and are not to be construed as a limitation of the scope thereof.

EXAMPLE 1

Into a quartz photochemical immersion reactor, having an optical path of 1 cm, there were introduced 350 g of the olefin of formula (I), containing, 2% of its isomer of formula (VII):

(VII)

The starting compound was subjected to ultraviolet radiation by means of a high pressure Hg-vapor lamp (Hanau TQ 150W).

In the course of the reaction it was possible to observe, by means of a gas-chromatographic analysis, a progressive decrease of the product of formula (I) and a simultaneous appearing of 2 new peaks in a ratio to each other of 3 to 2. After approximately a 200-hour irradiation, although the perfluorononene of formula (VII) initially contained in the starting product was still present, the conversion of the olefin of formula (I) resulted to be complete. The final mixture was subjected to gas-chromatographic analysis and revealed the following composition:

| perfluoroolefin of formula (IV) | 56% |
| perfluoroolefin of formula (V) | 38% |
| perfluoroolefin of formula (VII) | 6% |

The reaction raw product was purified by rectification on a column equipped with 90 plates. Isolated were the products of formula (IV) and (V), which boiled at 116° C. and 118° C. respectively.

The structure of the product was confirmed by NMR ($^{19}F, \delta$ CFCl$_3$), the results being as follows

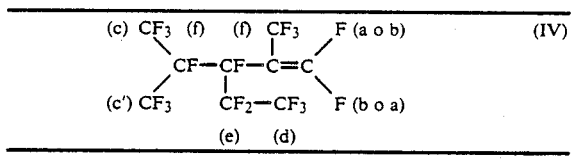

| a = | 54–55 ppm |
| b = | 59–62 ppm |
| c = | 69 ppm |
| c' = | 71 ppm |
| d = | 80–81 ppm |
| e = | 113–118 ppm |
| f = | 177–180 ppm |
| g = | 54 ppm |

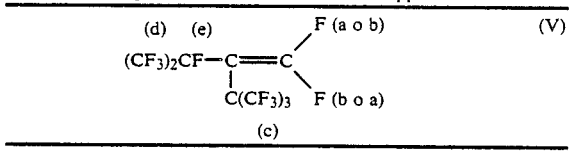

| a = | 49 ppm |
| b = | 51 ppm |
| c = | 61 ppm |
| d = | 74 ppm |
| e = | 170 ppm |

EXAMPLE 2

Into a tubular reactor having a diameter of 3.5 cm there were charged 370 g of a mixture consisting for 60% of the olefin of formula (IV) and for 40% of the olefin of formula (V) in order to have in the reactor a liquid height of about 20 cm. After having put the whole under a nitrogen atmosphere, a 1:1 mixture of N$_2$/F$_2$ (total flow of 2 l/h), and then pure F$_2$ (flow of 1 l/h) were bubbled thereinto, at an inner temperature of 30° C. Exothermicity of the reaction was observed and the trend thereof was followed by means of gas-chromatographic analysis; a progressive decrease of the peaks relating to the starting products was observed.

After 20 hours, while maintaining constant the F$_2$ flow equal to 1 l/h, the reaction was complete and the mixture resulted to be composed by the following three products:

| perfluoroalkane of formula (VIII) | 24% |
| perfluoroalkane of formula (IX) | 26% |
| perfluoroalkane of formula (VI) | 50%. |

Products (VIII), (IX) and (VI) were isolated by rectification on a 90 plates column and were subjected to NMR analysis ($^{19}F, \delta$ CFCl$_3$), which enabled to determine the structure. The results were as follows:

(CF$_3$)$_2$CF—CF$_2$—CF$_2$—CF$_3$    (VIII)
  (e)   (d)   (c)   (b)   (a)

| a = | 83 ppm |
| b = | 127 ppm |
| c = | 117 ppm |
| d = | 188 ppm |
| e = | 74 ppm |

(f)  (e)   (d)   (c)   (b)   (a)   (IX)
(CF$_3$)$_2$CFC(CF$_3$)$_2$—CF$_2$—CF$_2$—CF$_3$

| a = | 82 ppm |
| b = | 122 ppm |
| c = | 99 ppm |
| d = | 58 ppm |
| e = | 167 ppm |
| f = | 69 p |

(e)     (c)(b) (a)   (VI)
(CF3)3CCFCF(CF3)2
        |
       CF3
       (d)

| a = | 66–67 ppm |
| b, c = | 162–164 ppm |
| d = | 72 ppm |
| e = | 59 ppm |

EXAMPLE 3

30 g of the product of formula (V) were subjected to an analogous fluorination: obtained were high yields of the perfluoroalkane of formula (VI) and little amounts of products having a lower number of carbon atoms deriving from the rupture of the carbon-carbon single bonds.

EXAMPLE 4

The perfluoroalkane having formula (VI) was heated in sealed glass phials at different temperatures and times. The decomposition was followed by gas-chromatographic analysis and the results are showed hereinbelow:

| Time (h) | Temperatures (°C.) | % of product decomposed |
|---|---|---|
| 11 | 200 | 52 |
| 3,30 | 210 | 72 |
| 5 | 210 | 85 |
| 8 | 180 | 3 |

EXAMPLE 5

560 mg (1.2 m moles) of the perfluoroalkane of formula (VI) were loaded into a reactor having a volume of 30 ml and an inner diameter of 1 cm and after degasification 1.4 g of tetrafluorethylene were charged and heated at 100° C. for 1 hour and 20 minutes. Obtained are 1.4 g of polytetrafluoroethylene having a molecular weight of 145,000. 370 mg of the polymeric initiator are recovered.
We claim:
1. A process for the polymerization of ethylenically unsaturated monomers which comprises using a polymerization initiator selected from branched perfluoroalkanes having the formulas (VI) and (IX):
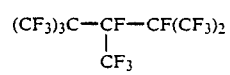  (VI)
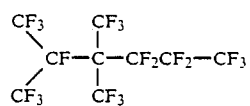  (IX)
* * * * *